United States Patent [19]

Baker et al.

[11] Patent Number: 5,554,629
[45] Date of Patent: Sep. 10, 1996

[54] 4-SUBSTITUTED 1,2,4-TRIAZOLE DERIVATIVES

[75] Inventors: Raymond Baker; Victor G. Matassa, both of Herts; Austin J. Reeve, Great Dunmow; Francine Sternfeld, London; Leslie J. Street, Harlow, all of England

[73] Assignee: Merck, Sharp & Dohme Ltd., Hoddesdon, England

[21] Appl. No.: 496,839

[22] Filed: Jun. 29, 1995

Related U.S. Application Data

[63] Continuation of Ser. No. 97,244, Jul. 23, 1993, abandoned.

[30] Foreign Application Priority Data

| Jul. 30, 1992 | [GB] | United Kingdom | 9216192 |
| Jul. 30, 1992 | [GB] | United Kingdom | 9216264 |
| Oct. 23, 1992 | [GB] | United Kingdom | 9222261 |

[51] Int. Cl.$^6$ .......... A61K 31/435; C07D 401/14; C07D 403/14
[52] U.S. Cl. .......... 514/323; 514/383; 546/201; 548/266.4
[58] Field of Search .......... 546/201; 548/266.4; 514/323, 383

[56] References Cited

U.S. PATENT DOCUMENTS

| 3,475,437 | 10/1969 | Landgraf et al. . |
| 3,644,403 | 2/1972 | Canas-Rodriguez et al. . |
| 3,801,594 | 4/1974 | Poletto et al. . |
| 4,138,570 | 2/1979 | Psaar . |
| 4,453,001 | 6/1984 | Brand et al. . |
| 4,618,617 | 10/1986 | Yamamoto . |
| 4,672,067 | 6/1987 | Coates et al. . |
| 4,692,531 | 9/1987 | Algieri et al. . |
| 4,839,377 | 6/1989 | Bays et al. . |
| 4,851,406 | 7/1989 | Mertens et al. . |
| 4,870,085 | 9/1989 | Glaser et al. . |
| 5,037,845 | 8/1991 | Oxford . |
| 5,225,431 | 7/1993 | Robertson et al. . |
| 5,298,520 | 3/1994 | Baker et al. .......... 548/266.4 |
| 5,451,588 | 9/1995 | Baker et al. .......... 514/323 |

FOREIGN PATENT DOCUMENTS

| 0200322A1 | 11/1986 | European Pat. Off. . |
| 313397 | 4/1988 | European Pat. Off. . |
| 0328200A1 | 8/1989 | European Pat. Off. . |
| 2083463 | 3/1982 | United Kingdom . |

OTHER PUBLICATIONS

"Characterization of a Novel 3H–5–Hydroxytryptamine Binding Site Subtype in Bovine Brain Membranes", Richard E. Heuring and Stephen J. Peroutka; The Journal of Neuroscience, Mar. 1987, vol. 7, pp. 894–903.

"Central Serotonin Receptors as Targets for Drug Research", Richard A. Glennon, Journal of Medicinal Chemistry, Jan. 1987, vol. 30, No. 1, pp. 1–12.

"Synthesis and Physicochemical Properties of 1,2,6,–Thiadiazine 1,1–Dioxides A Comparative Study with Pyrazoles", Jose Elguero, Carmen Ochoa, and Manfred Stud; Journal of Organic Chemistry, 1982, vol. 47, pp. 536–544.

"1,2,5–Thiadiazolidin–1,1–dioxid und Homologe", Michael Preiss; Chem. Ber., vol. 111, 1978, pp. 1915–1921.

"Nitroimidazoles: Part V–1–(1–Methyl–5–nitroimidazol–2–yl)–1,2,4–triazolidin–3,5–diones & Analogues", V. P. Arya, K. Nagarajan & S. J. Shenoy; Indian Journal of Chemistry, Oct. 1982, vol. 21B, pp. 941–944.

Heterocyclic Chemistry, A. R. Katritzky, et al., 1964, pp. 232–233.

Martin et al, "Analysis of the 5–HT Receptor, Etc" (Arch. Pharmacol.) (1990), 342, 111–119.

*Primary Examiner*—Patricia L. Morris
*Attorney, Agent, or Firm*—Robert J. North; Melvin Winokur

[57] ABSTRACT

A discrete class of 4-substituted 1,2,4-triazole derivatives are selective agonists of 5-HT$_1$-like receptors and are therefore useful in the treatment of clinical conditions, in particular migraine and associated disorders, for which a selective agonist of these receptors is indicated.

7 Claims, No Drawings

4-SUBSTITUTED 1,2,4-TRIAZOLE DERIVATIVES

CROSS REFERENCE TO RELATED APPLICATIONS

The instant application is a continuation case of Ser. No. 08/097,244, filed Jul. 23, 1993, now abandoned.

The present invention relates to a discrete class of 4-substituted 1,2,4-triazole derivatives which act on 5-hydroxytryptamine (5-HT) receptors, being selective agonists of so-called "5-HT$_1$-like" receptors. They are therefore useful in the treatment of clinical conditions for which a selective agonist of these receptors is indicated.

5-HT$_1$-like receptor agonists which exhibit selective vasoconstrictor activity have recently been described as being of use in the treatment of migraine (see, for example, A. Doenicke et al., *The Lancet*, 1988, Vol. 1, 1309–11). The compounds of the present invention, being selective 5-HT$_1$-like receptor agonists, are accordingly of particular use in the treatment of migraine and associated conditions, e.g. cluster headache, chronic paroxysmal hemicrania, headache associated with vascular disorders, tension headache and paediatric migraine.

EP-A-0313397 and WO-A-91/18897 describe separate classes of tryptamine derivatives substituted by various five-membered heteroaliphatic rings, which are stated to be specific to a particular type of "5-HT$_1$-like" receptor and thus to be effective therapeutic agents for the treatment of clinical conditions, particularly migraine, requiring this activity. However, neither EP-A-0313397 nor WO-A-91/18897 discloses or suggests the particular 4-substituted 1,2,4-triazole derivatives provided by the present invention.

EP-A-0497512, published on 5th Aug. 1992, describes a class of substituted imidazole, triazole and tetrazole derivatives which are stated to be selective agonists of 5-HT$_1$-like receptors and hence to be of particular use in the treatment of migraine and associated conditions.

The present invention provides a compound of formula I:

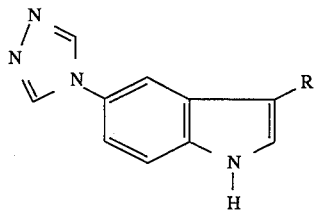

wherein R represents a 2-(dimethylamino)ethyl group, or a group of formula (i) or (ii):

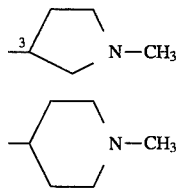

or a salt or prodrug thereof.

The compounds of formula I above have interesting biological activity, being potent and highly selective agonists of 5-HT$_1$-like receptors with good bioavailability. These compounds, and salts and prodrugs thereof, are generically encompassed within the scope of EP-A-0497512. However, EP-A-0497512 nowhere specifically discloses a 1,2,4-triazol-4-yl derivative, or a salt or prodrug thereof.

The compound of formula I above wherein R represents the group of formula (i) contains an asymmetric carbon atom at the 3-position of the pyrrolidine ring and is therefore optically active; for ease of reference, the relevant carbon atom has been designated by a "3" symbol in formula (i) above. As a consequence of possessing an asymmetric carbon atom within the molecule, this compound can exist as (R) and (S) enantiomers. The present invention accordingly includes within its scope the individual enantiomers of this compound, as well as mixtures thereof. One such mixture, the so-called racemic mixture or racemate, contains equal proportions of the individual (R) and (S) enantiomers. In addition, mixtures of this compound containing at least 75% of the enantiomer wherein the carbon atom in the 3-position of the pyrrolidine ring is in either the (R) or the (S) configuration and 25% or less of the opposite enantiomer are provided by the present invention, as also are mixtures containing at least 85% of one enantiomer and 15% or less of the opposite enantiomer. Desirably, the mixture is enriched to the extent that it contains at least 95%, preferably at least 99%, of one enantiomer and no more than 5%, preferably no more than 1%, of the opposite enantiomer.

For use in medicine, the salts of the compounds of formula I will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, fumaric acid, maleic acid, succinic acid, acetic acid, benzoic acid, oxalic acid, citric acid, tartaric acid, carbonic acid or phosphoric acid.

The present invention includes within its scope prodrugs of the compounds of formula I above. In general, such prodrugs will be functional derivatives of the compounds of formula I which are readily convertible in vivo into the required compound of formula I. Conventional procedures for the selection and preparation of suitable prodrug derivatives are described, for example, in "Design of Prodrugs", ed. H. Bundgaard, Elsevier, 1985.

Specific compounds within the scope of the present invention include:

(±)-N-methyl-3-[5-(1,2,4-triazol-4-yl)-1H-indol-3-yl]pyrrolidine;

3(R)-N-methyl-3-[5-(1,2,4-triazol-4-yl)-1H-indol-3-yl]pyrrolidine of formula IA:

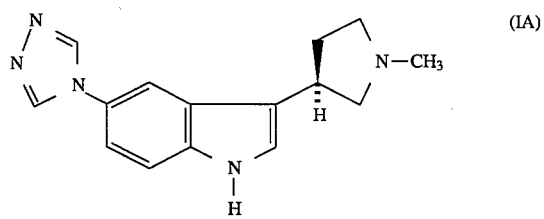

3(S)-N-methyl-3-[5-(1,2,4-triazol-4-yl)-1H-indol-3-yl-]pyrrolidine of formula IB:

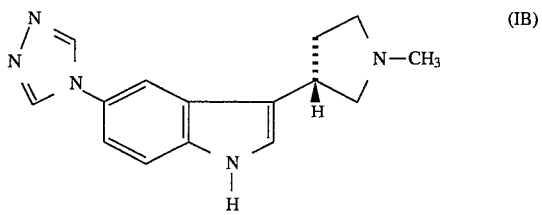

N-methyl-4-[5-(1,2,4-triazol-4-yl)-1H-indol-3-yl]piperidine of formula IC:

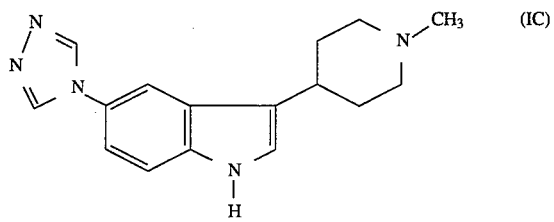

N,N-dimethyl-2-[5-(1,2,4-triazol-4-yl)-1H-indol-3-yl]ethylamine of formula ID:

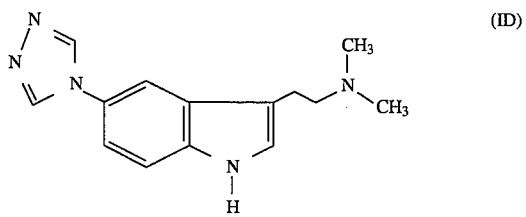

and salts and prodrugs thereof.

The invention also provides pharmaceutical compositions comprising one or more compounds of formula I above or a pharmaceutically acceptable salt thereof or a prodrug thereof in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral) parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone or gelatin.

In the treatment of migraine, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

The compounds of formula I above may be prepared by a process which comprises reacting the compound of formula II:

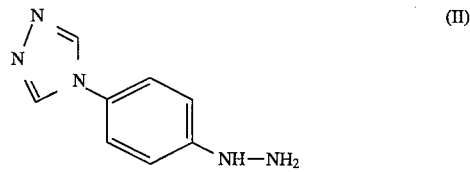

with a compound of formula III:

wherein R is as defined above; or a carbonyl-protected form thereof.

The reaction of compounds II and III may be carried out in a single step (Fischer indole synthesis) or by an initial non-cyclising step at a lower temperature to give a compound of formula IV:

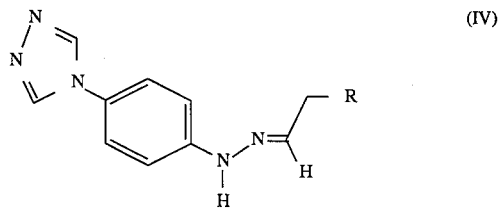

wherein R is as defined above; followed by cyclisation using a suitable reagent, such as a polyphosphate ester, to give a compound of formula I.

The compound of formula I above wherein R represents the group of formula (i) may alternatively be prepared in racemic form by a process which comprises the following steps:

(A) reaction of the compound of formula II with a compound of formula V, or a carbonyl-protected form thereof:

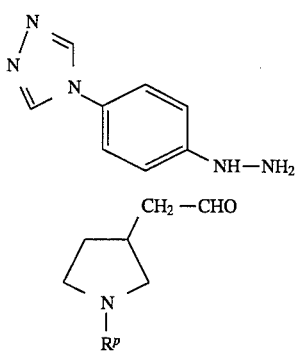

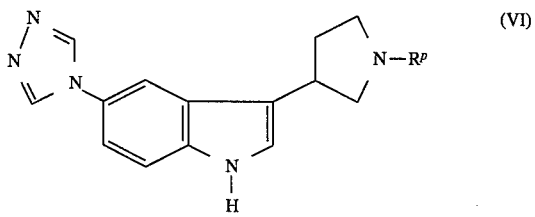

wherein R^P represents an amino-protecting group; to afford a compound of formula VI:

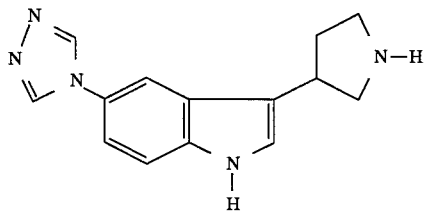

wherein R^P is as defined above;

(B) deprotection of the compound of formula VI thereby obtained, to afford a compound of formula VII:

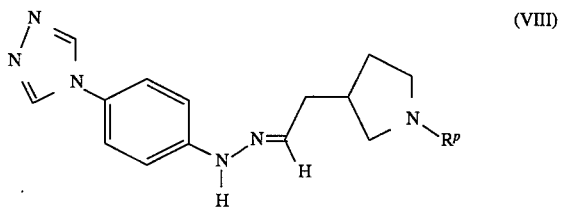

and (C) methylation of the compound of formula VII thereby obtained.

As with that between compounds II and III, the reaction between compounds II and V may be carried out in a single step (Fischer indole synthesis) or by an initial non-cyclising step at a lower temperature to give a compound of formula VIII:

(VIII)

wherein R^P is as defined above; followed by cyclisation using a suitable reagent, such as a polyphosphate ester, to give a compound of formula VI.

Suitable examples of amino-protecting groups for the substituent R^P include carboxylic acid groups such as chloroacetyl, trifluoroacetyl, formyl, benzoyl, phthaloyl, phenylacetyl or pyridinecarbonyl; acid groups derived from carbonic acid such as ethoxycarbonyl, benzyloxycarbonyl, t-butoxycarbonyl, biphenylisopropoxycarbonyl, p-methylbenzyloxycarbonyl, p-nitrobenzyloxycarbonyl, p-bromobenzyloxycarbonyl, p-phenylazobenzyloxycarbonyl, p-(p'-methoxyphenylazo)benzyloxycarbonyl or t-amyloxycarbonyl; acid groups derived from sulphonic acid, e.g. p-toluenesulphonic acid; and other groups such as benzyl, p-methoxybenzyl, trityl, o-nitrophenylsulphenyl or benzylidene.

The removal of the protecting group present in the resultant compound may be effected by an appropriate procedure depending upon the nature of the protecting group. Typical procedures include hydrogenation in the presence of a palladium catalyst (e.g. palladium carbon or palladium black) for benzyloxycarbonyl, p-nitrobenzyloxycarbonyl, p-bromobenzyloxycarbonyl, p-phenylazobenzyloxycarbonyl, p-(p'-methoxyphenylazo)benzyloxycarbonyl and trityl groups; treatment with hydrogen bromide in glacial acetic acid or trifluoroacetic acid for benzyloxycarbonyl, p-bromobenzyloxycarbonyl, p-phenylazobenzyloxycarbonyl and t-butoxycarbonyl groups; treatment with acetic acid and/or a mineral acid such as hydrochloric acid or sulphuric acid for trityl, t-butoxycarbonyl, formyl and benzylidene groups; and treatment with 2,3-dichloro-5,6-dicyano-1,4-benzoquinone for p-methoxybenzyl groups.

A particular amino-protecting group R^P is benzyl. Where benzyl is employed as the amino-protecting group R^P, a favoured method for its removal is hydrogenation. This may be conventional catalytic hydrogenation or, more particularly, the technique known as transfer hydrogenation. The latter procedure employs a hydrogenation catalyst such as palladium on carbon, ideally 10% palladium on carbon, in the presence of a hydrogen donor such as ammonium formate, sodium hypophosphite, triethylammonium formate or potassium formate, preferably ammonium formate. Where ammonium formate is employed as the hydrogen donor, the reaction is conveniently carried out in a solvent such as methanol or aqueous methanol, advantageously at a temperature in the region of 35°–45° C.

The individual enantiomers of the compound of formula I above wherein R represents the group of formula (i) may be prepared by resolution of racemic N-methyl-3-[5-(1,2,4-triazol-4-yl)-1H-indol-3-yl]pyrrolidine, prepared as described above, or a protected derivative thereof which may subsequently be deprotected by methods known per se at an appropriate subsequent stage. Known methods of resolution may suitably be employed, for example comprising the formation and separation of diastereoisomers. Suitable resolving agents include chiral acids which form acid addition salts with amino groups within the molecule. Suitable resolving acids are camphor derivatives, such as camphor-10-sulphonic acid, α-bromo-camphor-π-sulphonic acid, hydroxymethylene camphor and camphoric acid; menthol derivatives such as menthoxyacetic acid; naturally occurring optically active forms of tartaric acid and malic acid; and diacetyltartaric acid.

Alternatively, a chiral amino acid derivative may be employed in the resolution process, to form an amide bond, for example with the nitrogen atom at the 1-position of the indole nucleus, which subsequently may be cleaved under mild conditions. A suitable amino acid which may be employed is L-phenylalanine, optionally having its amino group protected.

The diastereoisomers are separated by conventional methods, such as chromatography or crystallisation. Suitable solvents for chromatography include ethyl acetate and petroleum ethers. Suitable solvents for crystallisation include non-polar solvents such as ether, methylene dichloride, petroleum ethers and methanol.

After separation, the appropriate diastereoisomer is converted to the enantiomer wherein the carbon atom at the 3-position of the pyrrolidine ring is in the requisite configuration, either (R) or (S) as required. If necessary, the diastereoisomer obtained wherein the carbon atom at the 3-position of the pyrrolidine ring is in the opposite configuration may be re-racemised for further resolution.

The individual enantiomers of the compound of formula I above wherein R represents the group of formula (i) may also be prepared by a chiral process which comprises the following steps:

(i) reaction of the compound of formula II with a compound of formula IX, or a carbonyl-protected form thereof:

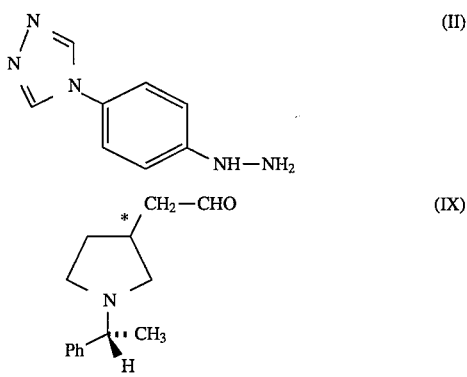

wherein the carbon atom designated * is in the (R) or (S) configuration; to afford a compound of formula X:

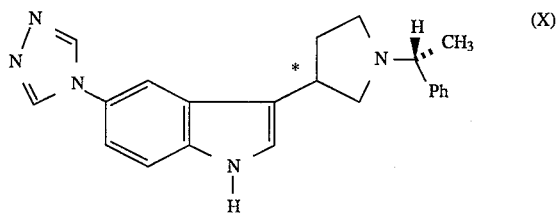

wherein the carbon atom designated * is in the (R) or (S) configuration;

(ii) deprotection of the compound of formula X thereby obtained, to a afford a compound of formula XI:

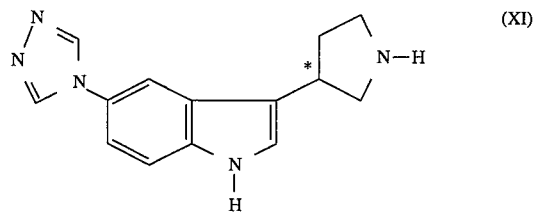

wherein the carbon atom designated * is in the (R) or (S) configuration; and (iii) methylation of the compound of formula XI thereby obtained.

Suitable carbonyl-protected forms of the compounds of formulae III, V and IX above include the dimethyl acetal derivatives.

As with that between compounds II and III, and between compounds II and V, the reaction between compounds II and IX may be carried out in a single step (Fischer indole synthesis) or by an initial non-cyclising step at a lower temperature to give a compound of formula XII:

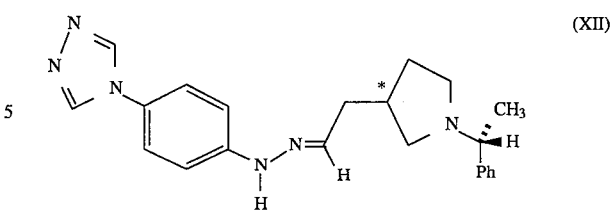

wherein the carbon atom designated * is in the (R) or (S) configuration; followed by cyclisation using a suitable reagent, such as a polyphosphate ester, to give a compound of formula X.

The hydrazine derivative of formula II may be prepared from the corresponding aniline derivative of formula XIII:

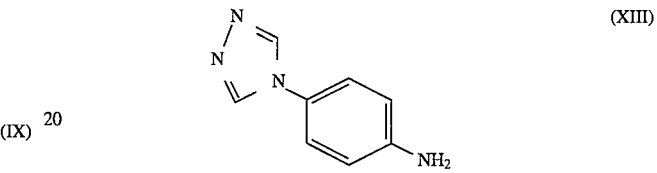

by diazotisation followed by reduction. Diazotisation is typically carried out using sodium nitrite/conc. HCl and the resulting diazo product reduced in situ using, for example, tin(II) chloride/conc. HCl, sodium sulphite/conc. HCl or sodium sulphite/conc. $H_2SO_4$.

The aniline derivative of formula XIII may suitably be prepared by reacting the hydrazine derivative of formula XIV with the acetanilide of formula XV:

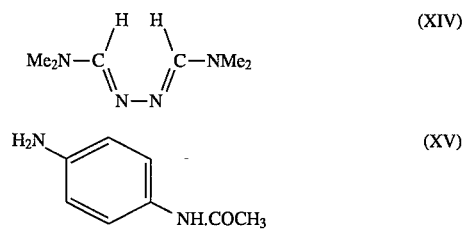

followed by removal of the N-acetyl protecting group.

The reaction between compounds XIV and XV is conveniently effected in refluxing toluene, advantageously in the presence of a catalytic quantity of p-toluenesulphonic acid. Subsequent removal of the N-acetyl protecting group is typically effected in hot aqueous hydrochloric acid.

The hydrazine derivative of formula XIV can be prepared from N,N'-diformylhydrazine by reaction with thionyl chloride/N,N-dimethylformamide, as reported in *J. Chem. Soc.* (C), 1967, 1664, and subsequent treatment with sodium methoxide in methanol.

The acetanilide of formula XV may be prepared by reduction of the corresponding nitro compound of formula XVI:

typically by transfer hydrogenation using a hydrogenation catalyst in the presence of a hydrogen donor such as ammonium formate, or alternatively by conventional catalytic hydrogenation or using tin(II) chloride.

The nitro compound of formula XVI is commercially available from Aldrich Chemical Company Ltd., Gillingham, United Kingdom.

The preparation of the aldehyde of formula III above wherein R represents the group of formula (ii) is illustrated by the following reaction scheme:

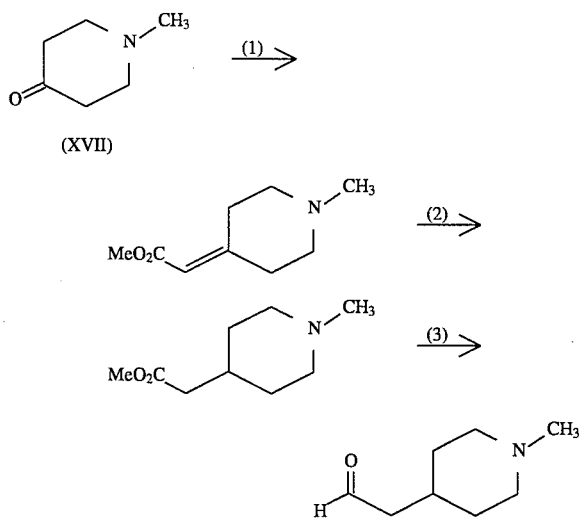

The starting compound XVII (1-methyl-4-piperidone) is commercially available from Aldrich Chemical Company Ltd., Gillingham, U.K. Step 1 of the reaction scheme involves reacting this compound with the Horner-Emmons reagent $MeO_2C \cdot CH_2 \cdot PO(OEt)_2$ in the presence of sodium hydride, using THF as the solvent. In Step 2, the double bond of the resulting piperidine olefin ester is hydrogenated over palladium-charcoal in ethanolic HCl. This is followed in Step 3 by reduction of the side-chain methyl ester group using diisobutylaluminium hydride (DIBAL-H) in THF, with subsequent Swern oxidation of the resulting terminal hydroxymethyl group to the aldehyde moiety present in the target intermediate of formula III.

The preparation of a typical intermediate of formula V above, wherein the amino-protecting group $R^P$ is benzyl, is illustrated by the following reaction scheme:

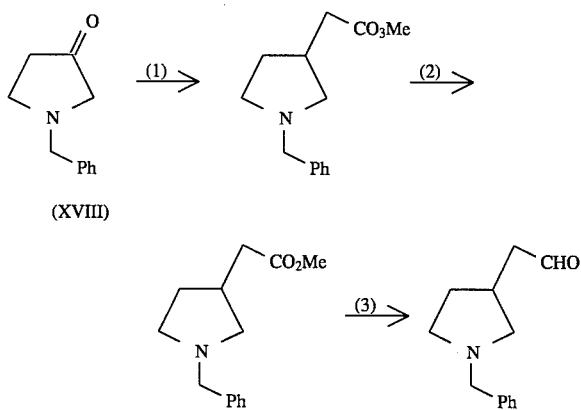

The starting compound XVIII (1-benzyl-3-pyrrolidinone) is commercially available from Aldrich Chemical Company Ltd., Gillingham, U.K. Step 1 of the reaction scheme involves reacting this compound with the Horner-Emmons reagent $MeO_2C \cdot CH_2 \cdot PO(OEt)_2$ in the presence of sodium hydride, using THF as the solvent. In Step 2, the double bond of the resulting pyrrolidine olefin ester is hydrogenated over palladium-charcoal in ethanolic HCl. This is followed in Step 3 by reduction of the side-chain methyl ester group using diisobutylaluminium hydride (DIBAL-H) in THF, with subsequent Swern oxidation of the resulting terminal hydroxymethyl group to the aldehyde moiety present in the target intermediate of formula V.

The aldehyde derivatives of formula IX above may be prepared by reduction of the corresponding cyano compound of formula XIX:

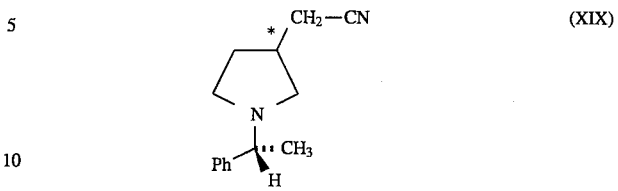

wherein the carbon atom designated * is in the (R) or (S) configuration. A suitable reducing agent for effecting this transformation is diisobutylaluminium hydride (DIBAL-H), and the reaction is conveniently carried out in tetrahydrofuran as solvent.

The preparation of both enantiomers of the cyano compound of formula XIX above is described in *J. Med. Chem.*, 1990, 33, 71.

Step (ii) of the above-described chiral process comprises the deprotection of the compound of formula X. Removal of the amino-protecting group is suitably effected by hydrogenation. This may be conventional catalytic hydrogenation or, more particularly, the technique known as transfer hydrogenation as described above.

Step (C) and step (iii) of the above-described processes comprise the methylation of the compounds of formulae VII and XI respectively. This is suitably effected by conventional N-methylation techniques, such as by treatment of compound VII or compound XI with formaldehyde in the presence of a reducing agent such as sodium cyanoborohydride.

The following Examples illustrate the preparation of compounds according to the invention.

The ability of test compounds to bind to $5\text{-}HT_1$-like receptors was measured in membranes prepared from pig caudate using the procedure described in *J. Neurosci.*, 1987, 7, 894. Binding was determined using 2 nM 5-hydroxytryptamine creatinine sulphate, $5\text{-}[1,2\text{-}^3H(N)]$ as a radioligand. Cyanopindolol (100 nM) and mesulergine (100 nM) were included in the assay to block out $5\text{-}HT_{1A}$ and $5\text{-}HT_{1C}$ binding sites respectively. The concentration of the compounds of the accompanying Examples required to displace 50% of the specific binding ($IC_{50}$) is below 1 µM in each case.

The activity of test compounds as agonists of the $5\text{-}HT_1$-like receptor was measured in terms of their ability to mediate contraction of the saphenous vein of New Zealand White rabbits, using the procedure described in *Arch. Pharm.*, 1990, 542, 111. Agonist potencies were calculated as $-\log_{10}EC_{50}$ ($pEC_{50}$) values, from plots of percentage 5-HT (1 µM) response against the concentration of the agonist. The compounds of the accompanying Examples were found to possess $pEC_{50}$ values in this assay of not less than 5.0 in each case.

EXAMPLE 1

(±)
N-Methyl-3-[5-(1.2.4-triazol-4-yl)-1H-indol-3-yl] pyrrolidine, 2.55 Oxalate

INTERMEDIATE 1

N-Benzyl-3-(formylmethyl)pyrrolidne
a) N-Benzyl-3-(carbomethoxymethyl)pyrrolidine
Methyl diethylphosphonoacetate (26.9 g, 0.128 mol) in THF (50 ml) was added dropwise to a stirred suspension of NaH (5.12 g, 60% dispersion in oil, 0.128 mol) in THF (125 ml), at 10° C. The mixture was stirred for 0.6h and a solution of N-benzyl pyrrolidin-3-one (20.4 g, 0.117 mol) in THF (50 ml) added dropwise. The mixture was heated at 50° C. for 3h before removing the solvent under vacuum and redissolving the residue in $CH_2Cl_2$ (300 ml) and $H_2O$ (100 ml). The $CH_2Cl_2$ phase was separated and washed with $H_2O$ (50 ml) and sodium bisulphite solution (2×50 ml) and dried ($Na_2SO_4$). The crude product was chromatographed on silica gel eluting with petroleum ether/ethyl acetate (60:40) to give a mixture of the unsaturated esters (24.7 g, 92%).

25 A solution of the preceding unsaturated ester (18.8 g, 81.4 mmol) in MeOH (95 ml) and 2NHCl (40 ml) was hydrogenated at 50 psi, over Pd-C (1.9 g), for 0.25h. The catalyst was removed by filtration through celite and the solvents removed under vacuum. The residue was basified with saturated $K_2CO_3$ solution (100 ml) and extracted with EtOAc (2×). The combined extracts were dried ($MgSO_4$) and evaporated and the residue chromatographed on silica gel, eluting with $CH_2Cl_2$/MeOH (96:4) to give the title-carbomethoxy ester (15.4 g, 81%); δ (360 MHz, $CDCl_3$) 1.40–1.49 (1H, m, CH of $CH_2$): 2.03–2.12 (1H, m, CH of $CH_2$), 2.18 (1H, dd, J=6.4 and 9.2 Hz, CH of $CH_2$), 2.40 (2H, d, J=7.5 Hz, C$\underline{H}_2$CO$_2$CH$_3$), 2.49–2.63 (3H, m, CH and $CH_2$), 2.80 (1H, dd, J=7.6 and 9.2 Hz, CH of $CH_2$), 3.59 (2H, ABq, J=13 Hz C$\underline{H}_2$ Ph), 3.65 (3H, s, $CH_3$), 7.21–7.31 (5H,m, Ar—H).

b) N-Benzyl-3-(formylmethyl)pyrrolidine

Diisobutylaluminium hydride (105 ml of a 1M solution in toluene, 0.105 mol) was added dropwise to a stirred solution of the preceding ester (7.0 g, 30.0 mmol) in toluene (400 ml) at −35° C., over a 0.5 h period. The solution was allowed to warm to room temperature, and stirred for 2 h, before quenching by addition of methanol (10 ml), 2 NNaOH (5 ml) and $H_2O$ (5 ml), sequentially. The mixture was stirred for 1 h and the resulting precipitate removed by filtration through celite. The solvent was removed under vacuum to give the desired ethyl alcohol (5.65 g, 92%).

Dimethylsulphoxide (1.66 ml, 23.4 mmol) was added dropwise to a solution of oxalyl chloride (1.49 g, 11.7 mmol) in $CH_2Cl_2$ (130 ml) at −75° C. The mixture was stirred for 0.25 h before adding a solution of the preceding alcohol (2.0 g, 9.76 mmol) in $CH_2Cl_2$ (30 ml) and stirring for 1 h, at −75° C. Triethylamine (4.94 g, 48.8 mmol) was added and the reaction mixture warmed to 25° C. and stirred for 1 h. Water (100 ml) and $CH_2Cl_2$ (400 ml) were added and the mixture basified with saturated $K_2CO_3$ solution. The aqueous phase was separated and extracted with $CH_2Cl_2$ (2×). The combined extracts were dried ($MgSO_4$) and evaporated and the residue chromatographed on silica gel eluting with $CH_2Cl_2$/EtOH (9:1) to give the desired aldehyde (1.63 g, 82%); δ (360 MHz, $CDCl_3$) 1.41–1.50 and 2.07–2.17 (2H, m, $CH_2$), 2.20 (1H, dd, J=5.9 and 9.1 Hz, CH of $CH_2$), 2.54–2.67 (5H, m, CH and 2 of $CH_2$), 2.80 (1H, dd, J=7.3 and 9.1 Hz, CH of $CH_2$), 3.60 (2H, ABq, J=13.0 Hz, $CH_2$), 7.22–7.31 (5H, m, Ar—H), 9.74 (1H, t, J=1.6 Hz, $\underline{H}$CO).

INTERMEDIATE 2

4-(1,2,4-Triazol-4-yl)phenylhydrazine a) 4'-Aminoacetanilide

A solution of 4-nitroacetanilide (5.0 g, 27.8 mmol) in EtOH-EtOAc (160 ml, 1:1), $H_2O$ (15 ml) and 5N HCl (5.6 ml, 28.0 mmol) was hydrogenated over 10% Pd-C (0.50 g) at 50 psi for 0.25 h. The catalyst was removed by filtration through celite and the solvents removed under vacuum. The free base was generated by dissolving the product in $H_2O$, basifying with 2N NaOH and extracting into EtOAc. The combined extracts were dried ($MgSO_4$) and evaporated to give the title-aniline (3.75 g, 90%); δ (250 MHz, $CDCl_3$/ $D_4$-MeOH) 2.10 (3H, s, $CH_3$), 6.68 (2H, d, J=8.8 Hz, Ar—H), 7.27 (2H, d, J=8.8 Hz, Ar—H).

b) 4'-(1,2,4-Triazol-4-yl)acetanilile

A mixture of the preceding aniline (3.52 g, 23.4 mmol), N,N-dimethylformamide azine (3.33 g, 23.4 mmol; *J. Chem. Soc C.* 1967, 1664) and p-toluenesulphonic acid monohydrate (0.223 g, 1.17 mmol), in anhydrous toluene (100 ml), was heated at reflux for 17 h. The beige coloured precipitate was filtered off and washed with toluene and $CH_2Cl_2$ and dried under vacuum to give the desired triazole (4.29 g, 91%); δ (250MHz, $D_4$-MeOH, $d_6$-DMSO) 2.14 (3H, s, $CH_3$), 7.60 (2H, d, J=8.8 Hz, Ar—H), 7.78 (2H, d, J=8.8 Hz, Ar—H), 8.96 (2H, s, Ar—H).

c) 4'-(1,2,4-Triazol-4-yl)aniline

A solution of the preceding acetanilide (4.91 g, 24.3 mmol) in 5N HCl(100 ml) was heated at 125° C. for 1.5 h. The mixture was cooled to 0° C., basified with conc. aqueous NaOH solution and extracted with $CH_2Cl_2$ (×5). The combined extracts were dried ($MgS_4$) and evaporated and the residue chromatographed on silica-gel eluting with $CH_2Cl_2$/MeOH/$NH_3$ (80:8:1) to give the title-aniline (2.94 g, 76%); δ (250MHz, $CDCl_3$) 3.80 (2H, s, $NH_2$), 6.71 (2H, d, J=8.8 Hz, Ar—H), 7.08 (2H, d, J=8.8 Hz, Ar—H), 8.36 (2H, s, Ar—H).

d) 4'-(1,2,4-Triazol-4-yl)phenylhydrazine

To a solution of the preceding aniline (1.60 g, 9.99 mmol) in conc. HCl/$H_2O$ (23 ml and 3 ml respectively) was added at −21° C., a solution of $NaNO_2$ (0.69 g, 9.99 mmol) in $H_2O$ (8 ml), at such a rate as to maintain the temperature below −10° C. The mixture was stirred for 0.3 h and then filtered rapidly through a sinter, under vacuum. The filtrate was added to a cooled (−20° C.) solution of $SnCl_2$.$2H_2O$ (9.02 g, 40.0 mmol) in conc. HCl (17 ml). The mixture was stirred at −20° C. for 0.25 h and then at room temperature for 1.25 h. The resulting solid was filtered off and washed with $Et_2O$ and dried under vacuum. The crude product was dissolved in $H_2O$, basified with conc aq. NaOH and extracted with EtOAc (×5). The combined extracts were dried ($MgSO_4$) and evaporated to afford the title-product (0.95 g, 54%); δ ($CDCl_3$/$D_4$-MeOH) 3.98 (3H, br s, NH and $NH_2$), 6.97 (2H, d, J=12.0 Hz, Ar—H), 7.25 (2H, d, J=12.0 Hz, Ar—H), 8.48 (2H, s, Ar—H).

(±)N-Benzyl-3-[5-(1,2,4-triazol-4-yl)1H-indol-3yl-]pyrrolidine

A solution of Intermediate 2 (0.416 g, 2.37 mmol) and Intermediate 1 (0.4 g, 1.96 mmol), in 4% $H_2SO_4$ (45 ml), was heated at reflux for 40 h. The mixture was cooled to room temperature and $CH_2Cl_2$ (100 ml) added and the aqueous basified (pH 12/13) with saturated $K_2CO_3$ solution. The aqueous layer was separated and extracted further with $CH_2Cl_2$ (×5). The combined extracts were dried ($MgSO_4$) and evaporated and the residue chromategraphed on silica gel, eluting with $CH_2Cl_2$/MeOH 9:1), to give the title-benzylpyrrolidine (0.183 g, 22.5%); (250 MHz, $CDCl_3$) 1.87–2.06 (1H, m, CH of $CH_2$), 2.30–2.43 (1H, m, CH of $CH_2$), 2.69–3.02 (4H, m, 2 of $CH_2$), 3.57–3.68 (1H, m, CH), 3.71 (2H, ABq, J=13 Hz, C$\underline{H}_2$Ph), 7.05–7.36 (7H, m, Ar—H), 7.46 (1H, d, J=8.5 Hz, Ar—H), 7.78 (1H, d, J=2.0 Hz, Ar—H), 8.46 (2H, s, Ar—H), 8.71 (1H, br s, NH).

(±)
N-H-3-[5-(1,2,4-Triazol-4-yl)-1H-indol-3-yl]pyrrolidine

A mixture of the preceding benzylpyrrolidine (0.183 g, 0.53 mmol), ammonium formate (0.176 g, 2.79 mmol) and 10%Pd-C (0.183 g), in MeOH (17 ml), was stirred at room temperature for 0.25 h and then at 70° C. for 0.9 h. The catalyst was removed by filtration through celite and the solvent removed under vacuum. The crude product was chromatographed on silica gel eluting with $CH_2Cl_2$/MeOH/$NH_3$ (20:8:1) to give the desired NH-pyrrolidine (99 mg, 73%); δ (360 MHz, $D_4$-MeOH) 1.82–1.95 and 2.16–2.30 (each 1H, each m, $CH_2$), 2.76–3.10 (3H, m, CH of $CH_2$ and $CH_2$), 3.24–3.50 (2H, m, CH of $CH_2$ and CH), 7.16 (1H, s, Ar—H), 7.17 (1H, dd, J=1.5 and 8.4 Hz, Ar—H), 7.42 (1H, d, J=8.4 Hz, Ar—H), 7.69 (1H, d, J=1.5 Hz, Ar—H), 8.80 (2H, s, Ar—H).

(±) N-Methyl-3-[5-(1,2,4-triazol-4-yl)-1H-indol-3-yl] pyrrolidine, 2.55 Oxalate

A solution of HCHO (35 mg of a 38% w/v solution; 0.44 mmol) in MeOH (8 ml) was added to a stirred solution of the preceding amine (90 mg, 0.36 mmol), $NaCNBH_3$ (28 mg, 0.45 mmol) and glacial acetic acid (0.05 ml, 0.89 mmol), in MeOH (8 ml), at 0° C. The mixture was stirred at 0° C. for 2 h and then at room temperature for 0.7 h. Saturated $K_2CO_3$ solution (6 ml) was added and the solvent removed under vacuum. The resulting residue was taken up into EtOAc (125 ml) and washed with brine (×2). The combined aqueous was re-extracted with EtOAc (×2) and the combined extracts dried ($MgSO_4$) and evaporated. Flash chromatography of the residue, eluting with $CH_2Cl_2$/MeOH/$NH_3$ (40:8:1), afforded the desired product (78 mg, 82%) and the 2.55 oxalate salt prepared; mp 40° C. (hygroscopic). Found: C, 48.84; H, 5.02; N, 13.60. $C_{15}H_{17}N_5$·2.5 $(C_2H_2O_4)$. 0.2 $H_2O$. 0.03 (EtOH). 0.03 ($Et_2O$) requires C, 48.51; H, 4.62; N, 14.02%. δ (360 MHz, $D_2O$) 2.26–2.44 and 2.58–2.76 (each 1H, each m, $CH_2$), 3.01 and 3.02 (total 3H, each s, $CH_3$), 3.22–4.16 (total 5H, 2 of $CH_2$ and CH), 7.39 (1H, dd, J=1.5 and 8.6 Hz, Ar—H), 7.46 and 7.49 (total 1H, each s, Ar—H), 7.67 (1H, d, J=8.6 Hz, Ar—H), 7.84 (1H, d, J=1.5 Hz, Ar—H), 9.28 (2H, s, Ar—H).

EXAMPLE 2

3(S)-N-Methyl-3-[5-(1,2,4-triazol-4-yl)-1H-indol-3-yl]pyrrolidine. Benzoate

INTERMEDIATE 3

3(S)-N-[(R)-1-Phenylethyl]-3-(formylmethyl)pyrrolidine a) 3(S)-N-[(R)-1-Phenylethyl]-3-(cyanomethyl)pyrrolidine Prepared from 3(R)-N-[(R)-1-phenylethyl]-3-(hydroxymethyl) pyrrolidine by literature procedures (*J. Med. Chem.* 1990, 33(1), 71).

b) 3(S)-N-[(R)-1-Phenylethyl]-3-(formylmethyl)pyrrolidine

Diisobutylaluminium hydride (37.4 ml of a 1M solution in toluene, 37.4 mmol) was added to a solution of the preceding nitrile (4.0 g, 18.7 mmol), in THF (100 ml), and the mixture stirred at room temperature for 3 h. Ethyl acetate (40 ml) and saturated $NH_4Cl$ solution (30 ml) were added and the mixture stirred for 0.25 h before adding 4% $H_2SO_4$ (10 ml) and allowing to stir for 0.5 h. The mixture was basified with $K_2CO_3$ solution and extracted with EtOAc (3×). The combined extracts were dried ($Na_2SO_4$) and evaporated and the crude product chromatographed on silica gel eluting with $CH_2Cl_2$/MeOH (9:1) to give the title aldehyde (2.3 g, 57%); δ (360 MHz, $CDCl_3$) 1.37 (3H, d,J=6.6 Hz, $CH_3$CH), 1.37–1.48 (1H, m, CH of $CH_2$), 2.02–2.12 (2H, m, CH and CH of $CH_2$), 2.39–2.46, 251–2.65 and 2.81–2.85 (1H, 4H and 1H respectively, each m, 3 of $CH_2$) 3.21 (1H, q, J=6.6 Hz, C$H$CH$_3$), 7.20–7.32 (5H, m, Ar—H).

3(S)-N-Methyl-3-[5-(1,2,4-triazol-4-yl)-1H-indol-3-yl]pyrrolidine, Benzoate.

The title compound was prepared from the hydrazine, Intermediate 2, and the aldehyde, Intermediate 3, using the procedures described for Example 1. The benzoate salt was prepared; mp 187°–190° C. Found: C, 68.11; H, 6.13; N, 18.11. $C_{15}H_{17}N_5$·$C_7H_6O_2$ requires C, 67.85; H, 5.95; N, 17.98%. δ (360 MHz, $D_2O$) 2.26–2.44 and 2.58–2.76 (each 1H, each m, $CH_2$), 3.03 (3H, s, $CH_3$), 3.22–4.16 (total 5H, 2 of $CH_2$ and CH), 7.34 (1H, dd, J=1.5 and 8.6 Hz, Ar—H), 7.46–7.57 (total 4H, m, Ar—H), 7.65 (1H, d, J=8.6 Hz, Ar—H), 7.76 (1H, d, J=1.5 Hz, Ar—H), 7.86–7.88 (2H, m, Ar—H) 8.82 (2H, s, Ar—H).

EXAMPLE 3

3(R)-N-Methyl-3-[5-(1,2,4-triazol-4-yl)-1H-indol-3-yl]pyrrolidine. Benzoate

The title compound was prepared from 3(R)-N-[(R)-1-phenylethyl]- 3-(cyanomethyl)pyrrolidine and Intermediate 2 using the procedures described for Example 1. The benzoate salt was prepared; mp 188°–189° C. Found: C, 68.12; H, 6.06; N, 18.10. $C_{15}H_{17}N_5$·$C_7H_6O_2$ requires C, 67.85; H, 5.95; N, 17.98%. δ (360 MHz, $d_6$-DMSO) 1.91–2.00 and 2.29–2.42 (each 1H, each m, $CH_2$), 2.42 (3H, s, $CH_3$), 2.60–2.88 (total 3H, m, $CH_2$ and CH of $CH_2$), 3.14–3.17 and 3.58–3.68 (each 1H, each m, CH of $CH_2$ and CH), 7.31 (1H, dd, J=1.5 and 8.6 Hz, Ar—H), 7.34 (1H, d, J=15.5 Hz, Ar—H), 7.44–7.50 and 7.54–7.59 (total 4H, each m, Ar—H), 7.85 (1H, d, J=1.5 Hz, Ar—H), 7.93–7.95 (2H, m, Ar—H), 9.02 (2H, s, Ar—H).

EXAMPLE 4

N-Methyl-4-[5-(1,2,4-triazol-4-yl)-1H-indol-3-yl]piperidine, Benzoate,

INTERMEDIATE 4

N-Methyl-4-(formylmethyl)piperidine a) N-Methyl-4-(carbomethoxymethylidenyl)piperidine Methyl diethylphosphonoacetate (88.69 g, 0.422 mol) was added dropwise to a stirred suspension of sodium hydride (18.56 g, 60% dispersion in oil, 0.464 mol) in THF (300 ml) under nitrogen, at such a rate as to maintain the temperature below 30° C. The mixture was stirred for 1 h and a solution of N-methyl-4-piperidinone (47.71 g, 0.422 mol) in THF (150 ml) was added dropwise. The mixture was heated at 60° C. for 4.5 h before removing the solvent under vacuum and redissolving the residue in dichloromethane (300 ml) and water (200 ml). The dichloromethane phase was separated, washed successively with water (200 ml) and saturated sodium bisulphite solution (2×70 ml) and dried ($MgSO_4$). The crude product was chromategraphed on silica gel, eluting with methanol/ether (5:95) to give the title-product (19.75 g, 28%). $^1H$ NMR (250 MHz, $CDCl_3$) δ (3H, s, N-$CH_3$), 2.35 (2H, t, J=6 Hz, $CH_2$), 2.40–2.50 (4H, m, 2 of $CH_2$), 3.00 (2H, t, J=6 Hz, $CH_2$), 3.70 (3H, s, $CO_2CH_3$), 5.65 (1H, s, vinyl CH).

b ) N-Methyl-4-(carbomethoxymethyl)piperidine

A solution of the preceding unsaturated ester (19.5 g, 0.115 mol) in MeOH (140 ml), $H_2O$ (28 ml) and 5N HCl (23.1 ml, 0.115 mol) was hydrogenated over 10% Pd-C (1.95 g) at 40 psi for 0.5 h. The catalyst was removed by filtration through celite and the solvents removed under vacuum. The free base was generated by dissolving the residue in $H_2O$ (70 ml), basifying with saturated $K_2CO_3$ solution and extracting into EtOAc. The combined extracts were dried ($MgSO_4$) and evaporated to give the title-ester (8.41 g; 43%). $^1H$ NMR (250 MHz, $CDCl_3$) δ1.24–1.37 (2H, m, $CH_2$), 1.69–1.81 (3H, m, $CH_2$ and CH), 1.94 (2H, td, J=11.9 and 2.2 Hz, $CH_2$), 2.23–2.26 (5H, m including s at δ2.26, $NCH_3$ and $CH_2$), 2.82 (2H, br d, J=11.6 Hz, $CH_2$), 3.67 (3H, s, $CO_2Me$).

c) N-Methyl-4-(2-hydroxyethyl)piperidine

Diisobutylaluminium hydride (120 ml of a 1M solution in toluene, 0.120 mol) was added dropwise to a stirred solution of the preceding ester (8.19 g, 0.047 mol) in toluene (350 ml) at −35° C. under nitrogen. The solution was allowed to warm to room temperature over 1 h, before recooling to −30° C. and quenching by addition of methanol (5 ml), water (5 ml) and 2N NaOH (5 ml), sequentially. The mixture was allowed to warm to room temperature and the resulting precipitate removed by filtration through celite. The solvent was removed under vacuum and the residue passed through a pad of alumina, eluting with methanol/dichloromethane (4:96) to give the title-product (5.51 g, 82%). $^1H$ NMR (360 MHz, $CDCl_3$) δ1.23–1.47 (3H, m, $CH_2$ and CH), 1.52 (2H, q, J=6.6 Hz, $CH_2$), 1.69 (2H, br d, J=13.0 Hz, $CH_2$), 1.91 (2H, td, J=11.5 and 2.1 Hz, $CH_2$), 2.18 (3H, s, $CH_3$), 2.83 (2H, br d, J=11.8 Hz, $CH_2$), 3.69 (2H, t, J=6.6 Hz, $CH_2$).

d) N-Methyl-4-(formylmethyl)piperidine

Dimethylsulphoxide (6.56 ml, 92.4 mmol) was added dropwise to a stirred solution of oxalyl chloride (4.03 ml, 46.2 mmol) in dichloromethane (300 ml) at −70° C. under nitrogen. The mixture was stirred for 0.2 h before adding a solution of the preceding alcohol (5.51 g, 38.5 mmol) in dichloromethane (80 ml) and stirring for 1 h at −70° C. Triethylamine (26.8 ml, 192 mmol) was added and the reaction mixture warmed to room temperature. Water and dichloromethane were added and the mixture basified with saturated $K_2CO_3$ solution. The aqueous phase was separated and extracted with dichloromethane (×4) and the combined extracts dried ($MgSO_4$) and evaporated. The crude product was chromatographed on alumina, eluting with methanol/dichloromethane (1:99) to afford the title-aldehyde (3.68 g, 69%); $^1H$ NMR (360 MHz, $CDCl_3$) δ1.35 (2H, qd, J=11.9 and 3.8 Hz, $CH_2$), 1.69–1.73 (2H, m, $CH_2$), 1.81–2.00 (3H, m, $CH_2$ and CH), 2.23 (3H, s, $CH_3$), 2.35–2.38 (2H, m, $CH_2$), 2.83 (2H, br d, J=11.9 Hz, $CH_2$), 9.78 (1H, t, J=2.0 Hz, CHO).

N-Methyl-4-[5-(1,2,4-trizol-4-yl)-1H-indol-3-yl] piperidine. Benzoate.

A solution of the dihydrochloride salt of Intermediate 2 (2.11 g, 8.5 mmol) and Intermediate 4 (1.0 g, 7.09 mmol) in 4% $H_2SO_4$ (100 ml) was heated at reflux for 22 h. The mixture was cooled to 0° C., basified with saturated $K_2CO_3$ solution and extracted into EtOAc (5×200 ml). The combined extracts were dried ($Na_2SO_4$), evaporated and the residue chromatographed on silica gel, eluting with $CH_2Cl_2$MeOH/$NH_3$ (60:8:1), to give the title-triazole (1.08 g, 54%). The monobenzoate salt was prepared; m.p. 218°–220° C. Found: C, 68.54; H, 6.12; N, 17.32. $C_{23}H_{25}N_5O_2$ requires C, 68.47; H, 6.25; N, 17.36%. $^1H$ NMR (360 MHz, $D_2O$) δ1.90–2.05 (2H, m, $CH_2$), 2.20–2.38 (2H, m, $CH_2$), 2.95 (3H, s, $CH_3$), 3.07–3.30 (3H, m, CH and $CH_2$), 3.58–3.72 (2H, m, $CH_2$), 7.26 (1H, dd, J=1.8 and 8.6 Hz, Ar—H), 7.35 (1H, s, Ar—H), 7.44–7.61 (4H, m, Ar—H), 7.71 (1H, d, J=1.8 Hz, Ar—H), 786–789 (2H, m, Ar—H), 8.94 (2H, s, Ar—H).

EXAMPLE 5

N,N-Dimethyl-2-[5-(1,2,4-trizol-4-yl)-1H-indol-3-yl]ethylamine. Benzoate.

A solution of the dihydrochloride salt of Intermediate 2 (1.50 g, 6.04 mmol) and 4-N,N-dimethylaminobutanol dimethylacetal (0.976 g, 6.05 mmol) in 4% aqueous sulphuric acid (120 ml) was stirred at room temperature for 2 h and then heated at reflux for 40 h. After cooling to room temperature, dichloromethane was added and the aqueous basified with saturated aqueous potassium carbonate solution. The aqueous was separated and extracted further with dichloromethane (×3). The combined organics were dried ($MgSO_4$), evaporated and the residue chromatographed on silica gel, eluting with $CH_2Cl_2$/MeOH/$NH_3$ (60:8:1), to give the title-triazole (0.70 g, 45%). The benzoate salt was prepared by addition of a solution of benzoic acid in diethyl ether to a solution of the triazole in methanol-diethyl ether. The solvent was removed under vacuum and the resultant product triturated with diethyl ether; mp 172°–174° C. Found: C, 66.59; H, 6.28; N, 18.42. $C_{21}H_{23}N_5O_2$ requires C, 66.83; H, 6.14; N, 18.55%). $^1H$ NMR (360 MHz, $D_2O$) δ2.95 (6H, s, $NMe_2$), 3.26 (2H, t, J=7.4 Hz, $CH_2$), 3.50 (2H, t, J=7.4 Hz, $CH_2$), 7.32 (1H, d, J=6.8 Hz, Ar—H), 7.46–7.55 (4H, m, Ar—H), 7.63 (1H, d, J=8.6 Hz, Ar—H), 7.73 (1H, s, Ar—H), 7.88 (2H, d, J=6.8 Hz, Ar—H), 8.81 (2H, s, Ar—H).

EXAMPLE 6

Tablet Preparation

Tablets containing 1.0, 2.0, 25.0, 26.0, 50.0 and 100 mg, respectively, of the following compounds are prepared as illustrated below:

(±)-N-Methyl-3-[5-(1,2,4-triazol-4-yl)-1H-indol-3-yl]pyrrolidine. 2.55 Oxalate

3(S)-N-Methyl-3-[5-(1,2,4-triazol-4-yl)-1H-indol-3-yl]pyrrolidine. Benzoate

3(R)-N-Methyl-3-[5-(1,2,4-triazol-4-yl)-1H-indol-3-yl]pyrrolidine. Benzoate

N-Methyl-4-[5-(1,2,4-triazol-4-yl)-1H-indol-3-yl]piperidine. Benzoate

N,N-Dimethyl-2-[5-(1,2,4-triazol-4-yl)-1H-indol-3-yl]ethylamine. Benzoate

| TABLE FOR DOSES CONTAINING FROM 1–25 MG OF THE ACTIVE COMPOUND | | | |
|---|---|---|---|
| | Amount (mg) | | |
| | 1.0 | 2.0 | 25.0 |
| Active Compound | | | |
| Microcrystalline cellulose | 49.25 | 48.75 | 37.25 |
| Modified food corn starch | 49.25 | 48.75 | 37.25 |
| Magnesium stearate | 0.50 | 0.50 | 0.50 |

| TABLE FOR DOSES CONTAINING FROM 26–100 MG OF THE ACTIVE COMPOUND | | | |
|---|---|---|---|
| | Amount (mg) | | |
| | 26.0 | 50.0 | 100.0 |
| Active Compound | | | |
| Microcrystalline cellulose | 52.0 | 100.0 | 200.0 |

17

-continued

TABLE FOR DOSES CONTAINING FROM
26–100 MG OF THE ACTIVE COMPOUND

| | Amount (mg) | | |
|---|---|---|---|
| Active Compound | 26.0 | 50.0 | 100.0 |
| Modified food corn starch | 2.21 | 4.25 | 8.5 |
| Magnesium stearate | 0.39 | 0.75 | 1.5 |

All of the active compound, cellulose, and a portion of the corn starch are mixed and granulated to 10% corn starch paste. The resulting granulation is sieved, dried and blended with the remainder of the corn starch and magnesium stearate. The resulting granulation is then compressed into tablets containing 1.0 mg, 2.0 mg, 25.0 mg, 26.0 mg, 50.0 mg and 100 mg of the active ingredient per tablet.

We claim:

1. A compound of formula I:

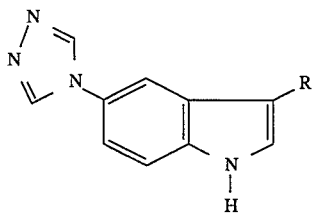

(I)

wherein R represents a 2-(dimethylamino)ethyl group or a group of formula (i) or (ii):

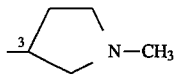

(i)

18

-continued

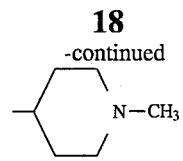

(ii)

or pharmaceutically acceptable salt thereof.

2. A compound selected from:
(±)-N-methyl-3-[5-(1,2,4-triazol-4-yl)-1H-indol-3-yl]pyrrolidine;
3(R)-N-methyl-3-[5-(1,2,4-triazol-4-yl)-1H-indol-3-yl]pyrrolidine;
3(S)-N-methyl-3-[5-(1,2,4-triazol-4-yl)-1H-indol-3-yl]pyrrolidine; and pharmaceutically acceptable salts thereof.

3. N-Methyl-4-[5-(1,2,4-triazol-4-yl)-1H-indol- 3-yl]piperidine, and pharmaceutically acceptable salt thereof.

4. The benzoate salt of N-methyl-4-[5-(1,2,4-triazol-4-yl)-1H-indol-3-yl]piperidine.

5. N,N-Dimethyl-2-[5-(1,2,4-triazol-4-yl)-1H-indol- 3-yl] ethylamine, and pharmaceutically acceptable salt thereof.

6. A pharmaceutical composition comprising an effective amount of a compound of formula I as defined in claim 1 or a pharmaceutically acceptable salt thereof in association with a pharmaceutically acceptable carrier.

7. A method for the treatment of migraine, cluster headache, chronic paroxysmal hemicrania, headache associated with vascular disorders, tension headache and pediatric migraine which method comprises administering to a patient in need of such treatment an effective amount of a compound of Formula I as defined in claim 1, or a pharmaceutically acceptable salt thereof.

\* \* \* \* \*